(12) United States Patent
Gruchatka et al.

(10) Patent No.: US 9,799,480 B2
(45) Date of Patent: Oct. 24, 2017

(54) CT SYSTEM

(71) Applicants: Herbert Gruchatka, Forchheim (DE); Ulrich Kühn, Baiersdorf (DE); Lothar Werner, Weißenohe/Dorfhaus (DE)

(72) Inventors: Herbert Gruchatka, Forchheim (DE); Ulrich Kühn, Baiersdorf (DE); Lothar Werner, Weißenohe/Dorfhaus (DE)

(73) Assignee: Siemens Aktiengesellschaft, München (DE)

( * ) Notice: Subject to any disclaimer, the term of this patent is extended or adjusted under 35 U.S.C. 154(b) by 325 days.

(21) Appl. No.: 14/660,189

(22) Filed: Mar. 17, 2015

(65) Prior Publication Data

US 2015/0270092 A1 Sep. 24, 2015

(30) Foreign Application Priority Data

Mar. 24, 2014 (DE) .................. 10 2014 205 393

(51) Int. Cl.
*H01J 35/10* (2006.01)
*A61B 6/03* (2006.01)
(Continued)

(52) U.S. Cl.
CPC ............ *H01J 35/106* (2013.01); *A61B 6/032* (2013.01); *A61B 6/035* (2013.01); *A61B 6/4488* (2013.01);
(Continued)

(58) Field of Classification Search
CPC ........... H01J 2235/1204; H01J 2235/12; H01J 2235/1225; H01J 35/106; A61B 6/032; A61B 6/035; A61B 6/4488; H05G 1/025
See application file for complete search history.

(56) References Cited

U.S. PATENT DOCUMENTS 6,477,231 B2    11/2002  Snyder et al.
2002/0146092 A1*  10/2002  Richardson ........... H01J 35/106
                                             378/130

(Continued)

FOREIGN PATENT DOCUMENTS

CN    1535099 A    10/2004
CN    1868026 A    11/2006
(Continued)

OTHER PUBLICATIONS

German Office Action cited in DE 10 2014 205 393.5, mailed Dec. 2, 2014, with English translation.
(Continued)

*Primary Examiner* — Glen Kao
(74) *Attorney, Agent, or Firm* — Lempia Summerfield Katz LLC

(57) ABSTRACT

The embodiments relate to a CT system with a stationary part and a rotatable part, which is supported rotatably in the stationary part. At least one x-ray tube unit cooled by a cooling fluid, an x-ray detector lying opposite the x-ray tube unit, and a cooling device coupled in terms of fluid technology to the x-ray tube unit via a coolant circuit are disposed in the rotatable part. A cooling air channel, through which cooling air is able to be fed into the rotatable part, and an exhaust air channel, through which heated exhaust air is able to be taken away from the rotatable part, are disposed in the stationary part. In accordance with the embodiments, at least one overpressure relief valve is disposed in the coolant circuit, through which the cooling fluid is able to be conveyed away in the exhaust air channel.

17 Claims, 3 Drawing Sheets

(51) Int. Cl.
*G01N 23/04* (2006.01)
*H01J 35/06* (2006.01)
*A61B 6/00* (2006.01)
*H05G 1/02* (2006.01)

(52) U.S. Cl.
CPC ............ *G01N 23/046* (2013.01); *H01J 35/06* (2013.01); *H05G 1/025* (2013.01); *H01J 2235/1225* (2013.01)

(56) References Cited

U.S. PATENT DOCUMENTS

| | | |
|---|---|---|
| 2004/0228450 A1 | 11/2004 | Mueller |
| 2005/0018817 A1 | 1/2005 | Oettinger et al. |
| 2005/0147208 A1* | 7/2005 | Kendall ................. H05G 1/025 378/141 |
| 2006/0188068 A1 | 8/2006 | Anno et al. |
| 2007/0053501 A1 | 3/2007 | Distler et al. |

FOREIGN PATENT DOCUMENTS

| | | |
|---|---|---|
| CN | 101115344 A | 1/2008 |
| DE | 10304661 A1 | 12/2004 |
| DE | 10342435 A1 | 5/2005 |
| DE | 102005041538 B4 | 4/2009 |

OTHER PUBLICATIONS

Chinese Office Action for related Chinese Application No. 201510113029.5 dated Mar. 3, 2017.

* cited by examiner

CT SYSTEM

CROSS-REFERENCE TO RELATED APPLICATIONS

This application claims the benefit of DE 10 2014 205 393.5, filed on Mar. 24, 2014, which is hereby incorporated by reference in its entirety.

TECHNICAL FIELD

The embodiments relate to a CT system.

BACKGROUND

A computed tomography (CT) system is described in DE 10 2005 041 538 B4. The known CT system includes a stationary part and a rotatable part that is supported rotatably in the stationary part. Disposed in the rotatable part are at least one x-ray tube unit cooled by a cooling fluid and an x-ray detector lying opposite the x-ray tube unit and also a cooling device coupled in terms of fluid technology via a cooling circuit to the x-ray tube unit. Disposed in the stationary part is a cooling air channel through which cooling air is able to be fed into the rotatable part. Furthermore, an exhaust air channel is disposed in the stationary part, through which the heated exhaust air is able to be discharged from the rotatable part.

The x-ray tube unit has a tube unit housing in which an x-ray tube is disposed. The x-ray tube includes a vacuum housing in which a cathode and an anode are disposed. The heat arising during the creation of the x-ray radiation within the x-ray tube is primarily taken up by the anode. The x-ray tube therefore has heat removed from it during operation by a circulating cooling fluid (e.g., oil or water). If, in this situation, a fracture occurs in the vacuum housing, cooling fluid reaches the hot anode and within a few seconds a large amount of steam may arise from the overheated cooling fluid. In order to overcome such a malfunction, collection containers and balancing containers are provided with air-cooled CT systems. This provides that a larger installation space is necessary and the constructional outlay is increased accordingly.

SUMMARY AND DESCRIPTION

The scope of the present invention is defined solely by the appended claims and is not affected to any degree by the statements within this summary. The present embodiments may obviate one or more of the drawbacks or limitations in the related art.

The object of the present embodiments is to create an air-cooled CT system with a compact and constructively-simple layout.

The CT system, in certain embodiments, includes a stationary part and a rotatable part that is rotatably supported in the stationary part. At least one x-ray tube unit cooled by a cooling fluid, an x-ray detector lying opposite the x-ray tube unit, and a cooling device coupled in terms of fluid technology to the x-ray tube unit via a cooling circuit are disposed in the rotatable part. Additionally, a cooling air channel through which cooling air is able to be fed into the rotatable part, and an exhaust air channel, through which the heated exhaust air is able to be removed from the rotatable part are disposed in the stationary part. In accordance with the embodiments, at least one overpressure relief valve is disposed in the coolant circuit through which the cooling fluid is able to be drained off into the exhaust air channel.

If a fracture occurs in the vacuum housing of the x-ray tube in the computed tomography system (CT system) during operation, the cooling fluid circulating in the x-ray tube unit housing gets onto the hot anode and from the overheated cooling fluid large amounts of steam occur within a few seconds. The pressure circumstances in the tube unit housing and in the coolant circuit as well as in the cooling device lead to the overpressure relief valve responding and the steam of the overheated cooling fluid escapes via the overpressure relief valve and is explicitly diverted into the exhaust air channel, via which the heated exhaust air is taken away.

The solution provides the steam to be taken away in a defined way via the exhaust air channel in a constructively-simple manner. Persons within the CT system (e.g., patients) or persons at the CT system (e.g., operating personnel) will not be endangered here. In addition the components of the CT system that lie outside the x-ray tube unit, (e.g., x-ray detector, high-voltage generator, and control electronics), are not damaged. A collection container or a balancing container, which increase the constructive outlay and would demand a larger installation space, are likewise not necessary.

The CT system thus has a compact and constructively-simple layout.

In accordance with one embodiment of the CT system, at least one overpressure relief valve is disposed on an anode-side part of the x-ray tube unit, e.g., in the area in which, in the event of a fracture of the vacuum housing, the pressure of the escaping cooling fluid is at its greatest and thus the steam formation is at its strongest.

As an alternative, or in addition, it may be advantageous for at least one overpressure relief valve to be disposed on the cooling device.

In accordance with a further advantageous embodiment, at least one overpressure relief valve is disposed in at least one cooling fluid line that runs between the x-ray tube unit and the cooling device. This embodiment is also able to be realized as an alternative or in addition.

By the realization of at least one of the forms of embodiment described above, depending on the respective constructional circumstances and the requirements imposed in each case, an optimum adaptation to the respective requirements is able to be realized by the person skilled in the art.

Should it not be possible, for constructional reasons, for example, to dispose the overpressure relief valve close enough to the exhaust air channel, it is advantageous to couple the overpressure relief valve with a steam-guidance pipe.

The solution is well suited for a CT system in which water is used as the cooling fluid for the x-ray tube unit. The cooling fluid may contain an additive. With water as a coolant, the additive is, for example, an anti-corrosion agent or a frost-protection agent.

In accordance with an embodiment, the cooling air is ambient air and the heated exhaust air is able to be discharged to the environment. An open air cooling system is thus involved, in which during operation the cooling of the components disposed in the rotatable part is done by a direct cooling and the heated exhaust air is discharged to the environment.

A likewise embodiment, which represents an alternative, is characterized in that the cooling air is able to be created via a heat exchanger from the heated air. A closed air cooling system is involved here, in which a heat exchanger is used to cool the hot exhaust air back down.

DETAILED DESCRIPTION

Figure 1:
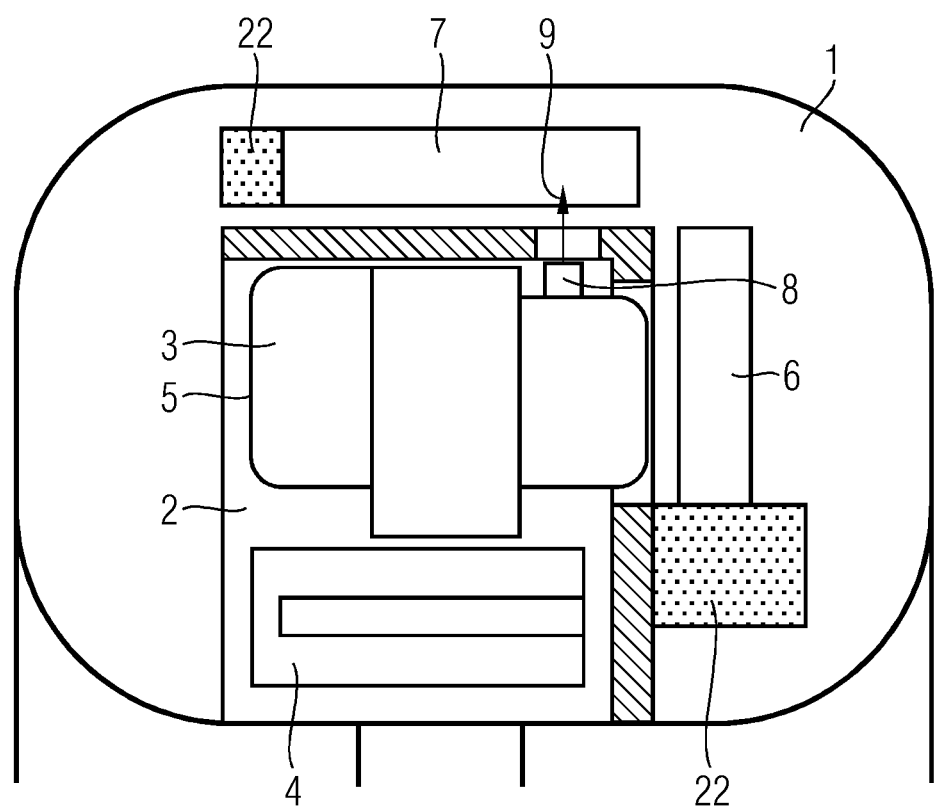
FIG. 1 depicts a section along the line I-I in the CT systems according to FIGS. 2 and 3.

The CT (computed tomography) system depicted in FIG. 1 includes a stationary part 1 and a rotatable part 2, which is supported rotatably via a rotation bearing 22 in the stationary part 1. Disposed in the rotatable part 2 are an x-ray tube unit 3 and a collimator 4. The x-ray tube unit 3 has an x-ray tube housing 5, in which an x-ray tube is disposed, which as a result of the presentation chosen is not visible. The x-ray tube includes a vacuum housing in which a cathode and an anode are disposed. The electrons created by the cathode are accelerated in the direction of the anode and create x-ray radiation when they strike the anode. The x-ray radiation exits from the x-ray tube unit 3 and passes through the collimator 4. After the radiation leaves the collimator 4, the x-ray radiation exits from the rotatable part 2 and irradiates an examination object (e.g., patient).

The heat occurring during the creation of the x-ray radiation within the x-ray tube is primarily taken up by the anode. The x-ray tube is therefore cooled during operation by a circulating cooling fluid. In the exemplary embodiments depicted in FIGS. 1 to 3, the cooling fluid is water.

Disposed in the stationary part of the CT system are a cooling air channel 6 and an exhaust air channel 7. Via the cooling air channel 6, cooling air is fed into the rotatable part 2. The cooling air cools the x-ray tube unit 3 and the collimator 4, (e.g., takes up heat), and subsequently enters the exhaust air channel 7 as heated exhaust air and then exits from the rotatable part 2.

If a fracture of the vacuum housing occurs during the operation of the x-ray tube unit 3, water gets onto the hot anode. Within a few seconds, a not inconsiderable part of the cooling fluid (e.g., water) evaporates and a large amount of steam arises inside the x-ray tube unit housing 5.

In order to discharge steam 9 arising during a fracture of the vacuum housing from the tube unit housing 5 in a defined manner, the CT system has at least one overpressure relief valve 8. In the exemplary embodiment depicted, a single overpressure relief valve 8 is disposed on an anode-side part of the x-ray tube unit 3. The steam 9 is conveyed away explicitly via the overpressure relief valve 8 into the exhaust air channel 7, via which the heated exhaust air is discharged.

Figure 2:
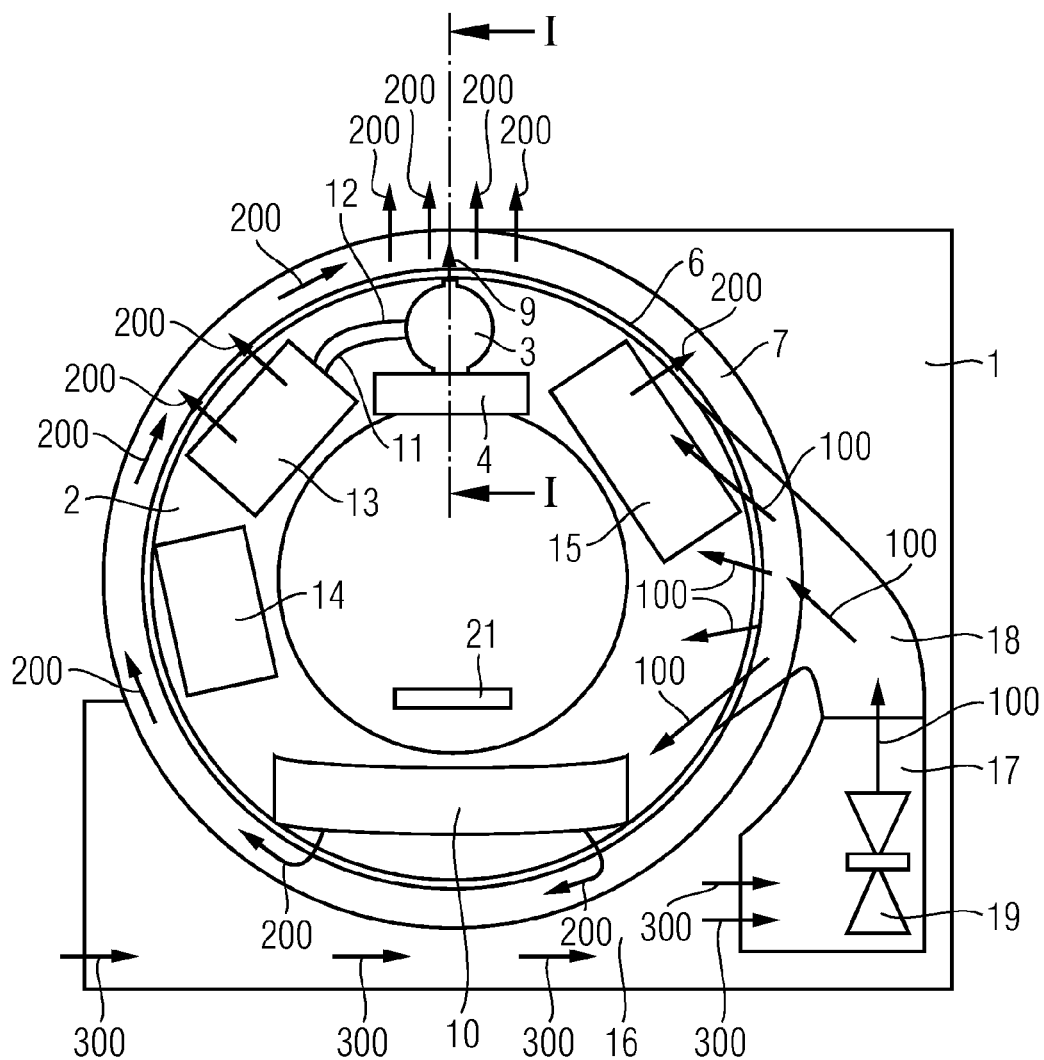
FIG. 2 depicts a first form of embodiment of a CT system.
Figure 3:
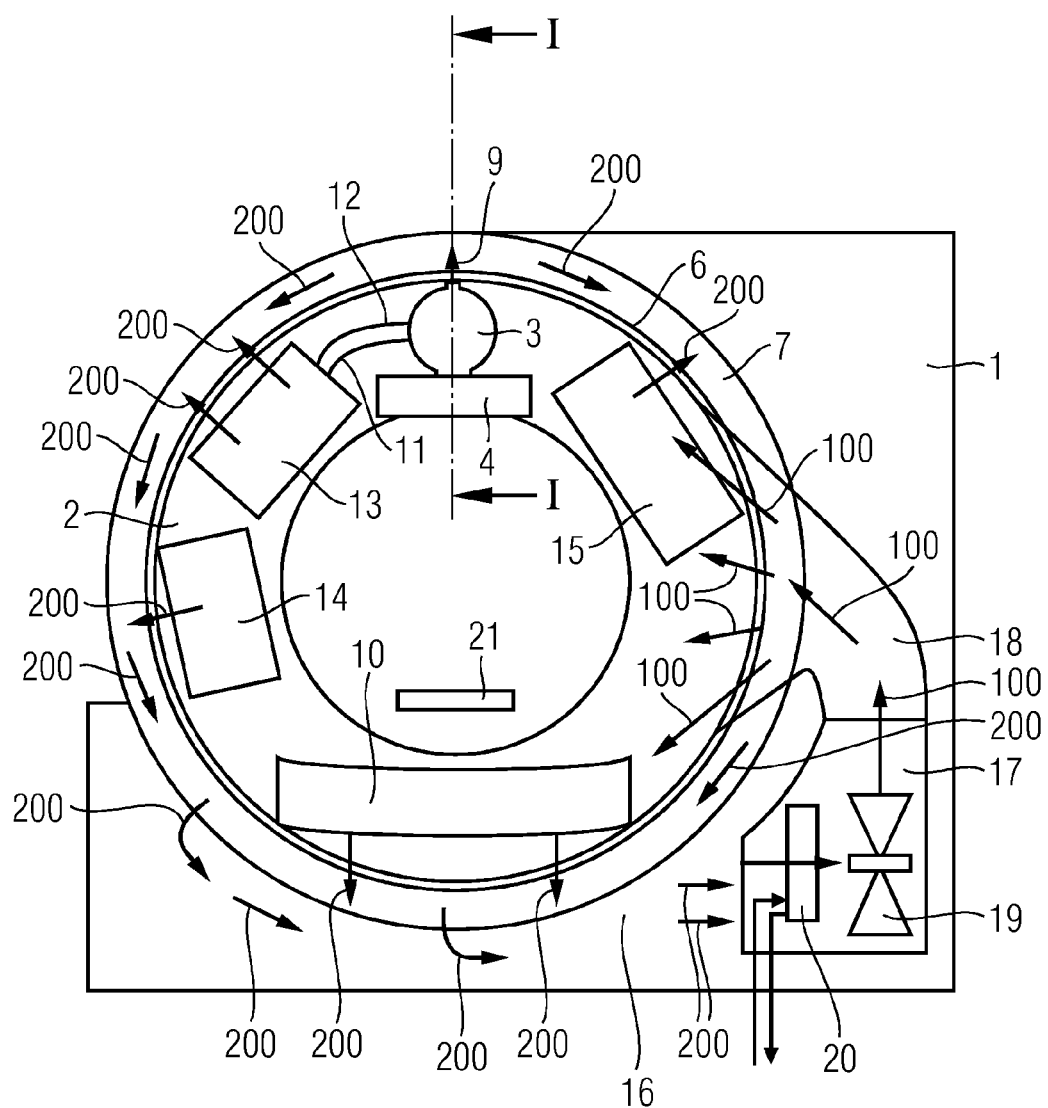
FIG. 3 depicts a second form of embodiment of a CT system.

FIGS. 2 and 3 each depict an air-cooled computed tomography system (CT system). The form of embodiment depicted in FIG. 2 involves a CT system with open air cooling, while the exemplary embodiment in accordance with FIG. 3 involves a CT system with closed air cooling.

In the CT system depicted in FIG. 2, the stationary part is once again labeled with the number 1 and the rotatable part supported rotatably in the stationary part 1 is labeled with the number 2.

Disposed in the rotatable part 2, as well as the x-ray tube unit 3 with the associated collimator 4 already described in FIG. 1, are an x-ray detector 10 lying opposite the x-ray tube unit 3, a cooling device 13 (radiant cooler) coupled in fluid technology terms to the x-ray tube unit 3 via a coolant feed line 11, and a coolant drainage line 12 as well as control electronics 14 and a high-voltage generator 15, which will also be referred to below as a whole as components 3 and 4 as well as 10 to 15.

Via the coolant feed line 11, the coolant is fed to the x-ray tube unit 2 and via the coolant drainage line 12 the heated cooling fluid is fed back into the cooling device 13.

The stationary part 1 is held by a force fit connection in the carrier body 16. Disposed in the carrier body 16 are a cooling module 17 and a feed channel 18.

The cooling model 17 contains a fan 19 that sucks in ambient air and blows said air in via the feed channel 18 as cooling air into the cooling air channel 6. This type of air cooling thus involves an open cooling system, in which the components 3 and 4 as well as 10 to 15 disposed in the rotatable part 2 are cooled directly during operation by ambient air.

The cooling air fed via the cooling air channel 6 into the rotatable part 2 (e.g., ambient air) cools the components 3 and 4 as well as 10 to 15 disposed in the rotatable part 2, such as the x-ray tube unit 3 and the cooling device 13. The cooling air here takes up heat and subsequently exits from the rotatable part 2 via the exhaust air channel 7 as heated exhaust air. The heated exhaust air is thus discharged to the environment.

Disposed within the rotatable part 2, in the beam path between the x-ray tube unit 3 and the x-ray detector 10, is a support table 21 on which an examination object (e.g., patient, workpiece, baggage) may be supported.

With the CT system in accordance with FIG. 3 once again, the stationary part is labeled 1 and the rotatable part is labeled 2. The rotatable part 2 is supported rotatably in the stationary part 1.

Disposed in the rotatable part 2, as well as the a x-ray tube unit 3 with the associated collimator 4 already described in FIG. 1, are once again an x-ray detector 10 lying opposite the x-ray tube unit 3, a cooling device 13 (e.g., radiant cooler) coupled in terms of fluid technology to the x-ray tube unit 3 via a coolant feed line 11 and a coolant drainage line 12 as well as control electronics 14 and a high-voltage generator 15, which will also be referred to below as a whole as components 3 and 4 and also 10 to 15.

The cooling fluid is fed via the coolant feed line 11 to the x-ray tube unit 2 and the heated cooling fluid is fed back via the coolant drainage line 12 into the cooling device 13.

The stationary part 1 is held by a force-fit connection in the carrier body 16. Disposed in the carrier body 16 are a cooling module 17 and a feed channel 18.

Disposed in the cooling module 17 are a fan 19 and also a heat exchanger 20. The fan 19 blows cooling air into the cooling air channel 6 via the feed channel 18.

The cooling air fed via the cooling air channel 6 into the rotatable part 2 cools the components 3 and 4 as well as 10 to 15 disposed in the rotatable part 2, such as the x-ray tube unit 3 and the cooling device 13. The cooling air takes up heat here and subsequently exits from the rotatable part 2 via the exhaust air channel 7 as heated exhaust air and is fed back into the cooling module 17. In the cooling module 17, a re-cooling of the heated exhaust air takes place in the heat exchanger 20. After the re-cooling of the heated exhaust air, the air is again available as cooling air for cooling the components 3 and 4 as well as 10 to 15 disposed in the rotatable part 2.

By contrast with the exemplary embodiment depicted in FIG. 2, this type of a cooling involves a closed air cooling system in which the re-cooling of the warm exhaust air is undertaken by a heat exchanger.

Disposed in the rotatable part 2 in the beam path between x-ray tube unit 3 and x-ray detector 10 is a support table 21 on which an examination object (e.g., patient, workpiece, baggage) may be supported.

Although the invention has been explained in greater detail by two exemplary embodiments, the invention is not restricted by the two exemplary embodiments depicted in FIGS. 1 to 3. Instead other variants of the inventive solution may be derived herefrom by the person skilled in the art without departing from the underlying inventive idea.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A CT system comprising:
   a stationary part; and
   a rotatable part supported rotatably in the stationary part,
   wherein at least one x-ray tube unit cooled by a cooling fluid, an x-ray detector lying opposite the x-ray tube unit, and a cooling device coupled to the x-ray tube unit via a coolant circuit are disposed in the rotatable part,
   wherein a cooling air channel, through which cooling air is able to be fed into the rotatable part, and an exhaust air channel, through which heated exhaust air is able to be taken away from the rotatable part, are disposed in the stationary part, and
   wherein at least one overpressure relief valve is disposed in the coolant circuit, through which the cooling fluid is configured to be conveyed away in the exhaust air channel.

2. The CT system as claimed in claim 1, wherein the at least one overpressure relief valve is disposed on an anode-side part of the x-ray tube unit.

3. The CT system as claimed in claim 1, wherein the at least one overpressure relief valve is disposed on the cooling device.

4. The CT system as claimed in claim 1, wherein the at least one overpressure relief valve is disposed in at least one cooling fluid line that runs between the x-ray tube unit and the cooling device.

5. The CT system as claimed in claim 1, wherein the overpressure relief valve is coupled to a steam-carrying pipe.

6. The CT system as claimed in claim 1, wherein the cooling fluid comprises water.

7. The CT system as claimed in claim 6, wherein the cooling fluid further comprises an anti-corrosion agent as an additive.

8. The CT system as claimed in claim 6, wherein the cooling fluid further comprises a frost-protection agent as an additive.

9. The CT system as claimed in claim 1, wherein the cooling fluid comprises an additive.

10. The CT system as claimed in claim 9, wherein the additive is an anti-corrosion agent.

11. The CT system as claimed in claim 9, wherein the additive is a frost-protection agent.

12. The CT system as claimed in claim 1, wherein the cooling air is ambient air and the heated exhaust air is configured to be discharged to an environment.

13. The CT system as claimed in claim 12, wherein the cooling air is configured to be created via a heat exchanger from the heated exhaust air.

14. The CT system as claimed in claim 1, wherein the cooling air is configured to be created via a heat exchanger from the heated exhaust air.

15. The CT system as claimed in claim 1, wherein at least one additional overpressure relief valve is disposed on an anode-side part of the x-ray tube unit.

16. The CT system as claimed in claim 1, wherein at least one additional overpressure relief valve is disposed on the cooling device.

17. The CT system as claimed in claim 1, wherein at least one additional overpressure relief valve is disposed in at least one cooling fluid line that runs between the x-ray tube unit and the cooling device.

* * * * *